(12) United States Patent
Koike

(10) Patent No.: US 8,740,814 B2
(45) Date of Patent: Jun. 3, 2014

(54) GUIDEWIRE

(75) Inventor: Tadahiro Koike, Nagoya (JP)

(73) Assignee: Asahi Intecc Co., Ltd., Nagoya-shi (JP)

( * ) Notice: Subject to any disclaimer, the term of this patent is extended or adjusted under 35 U.S.C. 154(b) by 31 days.

(21) Appl. No.: 13/461,465

(22) Filed: May 1, 2012

(65) Prior Publication Data
US 2013/0006221 A1    Jan. 3, 2013

(30) Foreign Application Priority Data

Jun. 30, 2011  (JP) ................... 2011-146508

(51) Int. Cl.
*A61B 5/00* (2006.01)
(52) U.S. Cl.
USPC ........................................ 600/585
(58) Field of Classification Search
USPC ........................................ 600/585
See application file for complete search history.

(56) References Cited

U.S. PATENT DOCUMENTS

| | | |
|---|---|---|
| 4,634,042 A | 1/1987 | Smith |
| 2004/0167442 A1 | 8/2004 | Shireman et al. |

FOREIGN PATENT DOCUMENTS

| | | |
|---|---|---|
| JP | U-H06-81547 | 11/1994 |
| JP | A-07-148267 | 6/1995 |
| JP | A-2001-152274 | 6/2001 |
| JP | A-2007-009334 | 1/2007 |
| JP | A-2007-135645 | 6/2007 |
| JP | A-2008-205265 | 9/2008 |
| WO | WO 99/65558 | 12/1999 |

OTHER PUBLICATIONS

Feb. 15, 2013 Office Action issued in Japanese Patent Application No. 2011-146508 (w/translation).
Aug. 27, 2012 Search Report issued in European Patent Application No. 12 169 901.1.
Japanese Office Action issued in Japanese Patent Application No. 2011-146508 dated Nov. 26, 2013 (w/translation).
Chinese Office Action issued in Chinese Patent Application No. 201210083602.9 dated Jan. 30, 2014 (w/ translation).

*Primary Examiner* — Max Hindenburg
(74) *Attorney, Agent, or Firm* — Oliff PLC

(57) ABSTRACT

A guidewire includes a core shaft, a coil body that covers the core shaft, and a joining portion formed of metal solder that couples the core shaft and the coil body. The coil body includes a tungsten wire and a noble metal plating layer that covers at least a portion of a surface of the tungsten wire. A surface of the noble metal plating layer has a first uneven shape, including at least one recess and at least one protrusion.

4 Claims, 5 Drawing Sheets

GUIDEWIRE

CROSS-REFERENCE TO RELATED APPLICATION

This application claims priority to Japanese Patent Application No. 2011-146508 filed in the Japan Patent Office on Jun. 30, 2011, the entire contents of which are incorporated herein by reference.

BACKGROUND

The disclosed embodiments relate to a medical device. More specifically, the disclosed embodiments related to a guidewire. Hitherto, various guidewires used for guiding, for example, medical devices to desired locations by being inserted into body tissues or tubes such as blood vessels, alimentary canals, or ureters, have been proposed.

For example, Japanese Unexamined Utility Model Registration Application Publication No. 6-81547 (Patent Document 1) discusses a guidewire in which a biocompatible material (gold, platinum, or fluorocarbon resin) covers a surface of a tungsten coil.

In addition, Japanese Unexamined Patent Application Publication 2001-152274 (Patent Document 2) discusses a tungsten material having an uneven shape and excellent secondary workability.

SUMMARY

In the guidewire discussed in Patent Document 1, wettability with respect to metal solder for joining a core shaft and a tungsten coil is improved by noble metal plating. However, the bonding strength between the core shaft and the coil body is not sufficient because a surface of the coil body is flat, as a result of which the coil body may separate from the core shaft.

When a tungsten wire having recesses and protrusions as discussed in Patent Document 2 is used in a coil body of a guidewire, because a surface of the tungsten wire having poor wettability with respect to metal solder has recesses and protrusions, the surface of the tungsten wire has poorer wettability in terms of surface chemistry. As a result, the bonding strength between a core shaft and the coil body formed of the tungsten wire is considerably reduced. This may cause the coil body to separate from the core shaft.

Accordingly, in view of such problems, it is an object of the present invention to provide a guidewire that makes it possible to prevent a coil body from separating from a core shaft by increasing the bonding strength between the core shaft and the coil body formed of a tungsten wire.

According to an aspect of the present invention, there is provided a guidewire including a core shaft, a coil body that covers the core shaft, and a joining portion formed of metal solder that joins the core shaft and the coil body. The coil body includes a tungsten wire and a noble metal plating layer that covers a surface of the tungsten wire. A surface of the noble metal plating layer has a first uneven shape.

In the guidewire according to the aspect of the present invention, the coil body includes a tungsten wire and a noble metal plating layer that covers a surface of the tungsten wire, with a surface of the noble metal plating layer having a first uneven shape. Therefore, wettability between metal solder and the coil body including tungsten is considerably increased. In addition, the first uneven shape causes an anchoring effect to occur. Consequently, it is possible to increase the bonding strength between the core shaft and the coil body, and, thus, prevent the coil body from separating from the core shaft.

DETAILED DESCRIPTION OF EMBODIMENTS

Figure 1A:
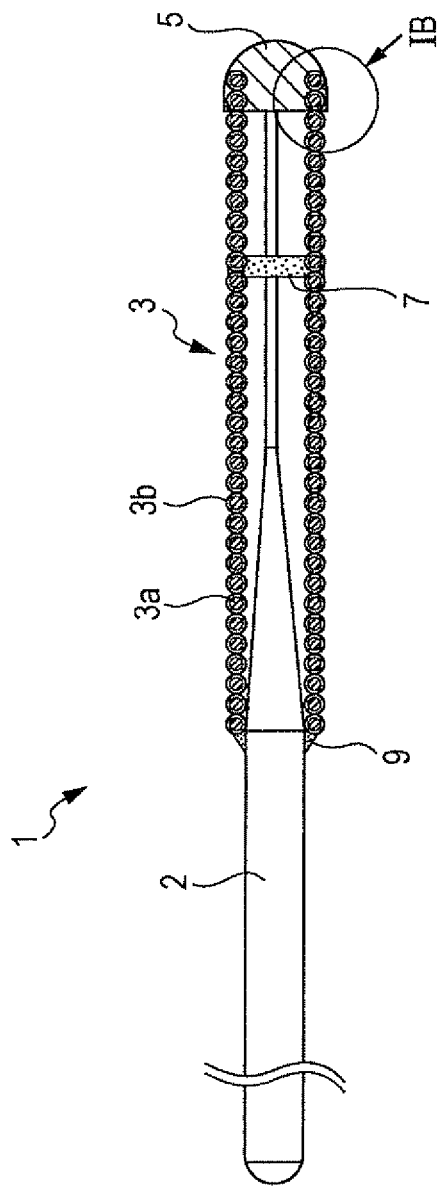
FIGS. 1A and 1B illustrate a structure according to an embodiment of the present invention, with FIG. 1A being an overall view of a guidewire and FIG. 1B being an enlarged longitudinal cross-sectional view of only wires of a coil body at a portion IB shown in FIG. 1A.

Guidewires according to the present invention will be described on the basis of the embodiments shown in the drawings.

Figure 1B:
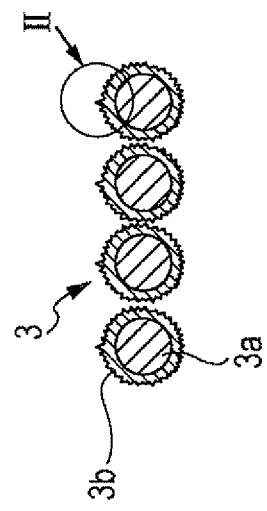

In FIGS. 1A and 1B, for convenience of explanation, the left side is described as being a proximal end and the right side is described as being a distal end.

In FIG. 1A, for facilitating understanding, a lengthwise direction of the guidewire 1 is reduced, and the entire guidewire 1 is schematically illustrated, so that the dimensions of the entire guidewire 1 differ from the actual dimensions thereof.

In FIG. 1A, the guidewire 1 includes a core shaft 2 and a coil body 3 that covers a distal end of the core shaft 2. The core shaft 2 and the coil body 3 are secured to each other by a tip portion 5, an intermediate joining portion 7, and a proximal-end joining portion 9.

FIG. 1B is an enlarged longitudinal cross-sectional view of a portion IB shown in FIG. 1A. For convenience of explanation, only wires of the coil body 3 are shown, that is, the wires without the tip portion are shown. FIG. 1A is a vertical sectional view of the coil body 3. Since the coil body 3 is formed by winding coil wires, the coil wires of the coil body 3 are in a state in which they are viewed in transverse cross section. Here, when FIG. 1B is viewed, the coil wires of the coil body 3 each include a tungsten wire $3a$ and a noble metal plating layer $3b$ that covers an outer periphery of the tungsten wire $3a$. The surface of each noble metal plating layer $3b$ has a first uneven shape.

Figure 2A:
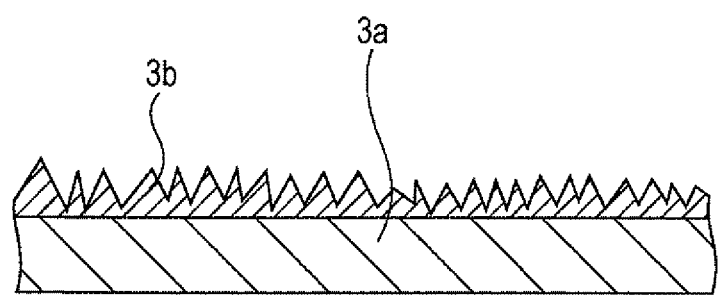
FIGS. 2A and 2B illustrate the structure according to embodiment of the present invention, with FIG. 2A being an enlarged view of a portion II shown in FIG. 1B and FIG. 2B illustrating a modification of the embodiment and being an enlarged view of the portion H shown in FIG. 1B.

FIG. 2A is an enlarged view of a portion II shown in FIG. 1B (that is, an enlarged view of one of the coil wires in transverse cross section). For convenience of explanation, the coil wire is shown as having a flat surface instead of an arc-shaped surface. In the embodiment, as shown in FIG. 2A, the surface of the tungsten wire 3a is smooth, and only the surface of the noble metal plating layer 3b is uneven (has the first uneven shape).

Accordingly, in the guidewire 1 according to the embodiment, the coil wires of the coil body 3 include the tungsten wires 3a and the corresponding noble metal plating layers 3b that cover the surfaces of the corresponding tungsten wires 3a. In addition, the surface of each noble metal plating layer 3b has the first uneven shape. Therefore, it is possible to considerably improve wettability between metal solder and the coil body 3 including the tungsten wires 3a, and to increase the bonding strength between the core shaft 2 and the coil body 3, and thus prevent the coil body 3 from separating from the core shaft 2 by an anchoring effect caused by the first uneven shape.

Next, the materials of the structural parts will be described.

Examples of the material of the core shaft 2 which may be used include stainless steel (such as SUS302, SUS304, and SUS316), superelastic alloys (such as Ni—Ti alloys), piano wires, nickel-chromium alloys, cobalt alloys, and other publicly known materials.

From the viewpoints of biocompatibility and wettability with respect of metal solder, preferred examples of the material of the noble metal plating layers 3b that cover the corresponding tungsten wires 3a include gold plating layers and platinum plating layers. From the viewpoint of manufacturing costs, gold plating layers are most desirable. Examples of other noble metals that may be used for plating are iridium, rhodium, palladium, and ruthenium.

Examples of the materials of the tip portion 5, the intermediate joining portion 7, and the proximal-end joining portion 9 include metal solder. Examples of metal solder include Sn—Zn—Al alloy solder, Sn—Ag—Cu alloy solder, Sn—Ag alloy solder, Sn—Cu alloy solder, Au—Sn alloy solder, Au—Si alloy solder, and Sn—Ag—Cu—In alloy solder. Additional materials, other than these materials may also be used.

Further, in addition to the embodiment described above, the metal solder according to the present invention includes an alloy solder such as silver solder having a relatively high melting point.

When joining the core shaft 2 and the coil body 3 using metal solder, flux is previously applied to a portion where the core shaft 2 and the coil body 3 are to be joined, or flux is previously applied to the metal solder, to considerably improve wettability of the metal solder with respect to the core shaft 2 and the coil body 3, thereby making it possible to further increase bonding strength between the core shaft 2 and the coil body 3.

The guidewire 1 according to the embodiment can be manufactured by the following method.

First, an outer periphery of a distal end portion of a core shaft 2 is ground by a centerless grinding machine, to manufacture the core shaft 2 whose distal end portion has a smaller outside diameter.

Next, tungsten wires 3a of the coil body 3 are subjected to grinding, degreasing, oxide-film removal, neutralization, water treatment, etc. Then, the tungsten wires 3a are plated with a noble metal by, for example, electroplating, so that the outer periphery of each tungsten wire 3a is covered with a noble metal plating layer 3b, to form each coil wire.

Next, by blasting and grinding the coil wires, the surfaces of the coil wires, that is, the surfaces of the noble metal plating layers 3b are formed with a first uneven shape. Then, the coil wires are wound around a cored bar for a coil, to form the coil body 3.

Then, a distal end of the core shaft 2 is inserted from a proximal end of the coil body 3, and the proximal end of the coil body 3 and the core shaft 2 are joined together using metal solder, to form a proximal-end joining portion 9.

Next, the distal end of the core shaft 2 and a distal end of the coil body 3 are joined using metal solder, to form a tip portion 5.

Next, an intermediate portion of the core shaft 2 and an intermediate portion of the coil body 3 are joined using metal solder, to form an intermediate joining portion 7. Lastly, by adjusting the shapes of the tip portion 5, and the joining portions, that is, the intermediate joining portion 7 and the proximal-end joining portion 9, with a grinding instrument, such as Leutor, it is possible to manufacture the guidewire 1.

The manufacturing method of the guidewire 1 is not limited to this manufacturing method, so that other methods and means may be used to manufacture the guidewire.

The noble metal plating layers 3b of the coil body 3 may be plating layers with the tungsten wires 3a being exposed. However, considering the wettability with respect to the metal solder, it is desirable that the entire peripheries of the tungsten wires 3a be covered by the noble metal plating layers 3b.

Figure 2B:
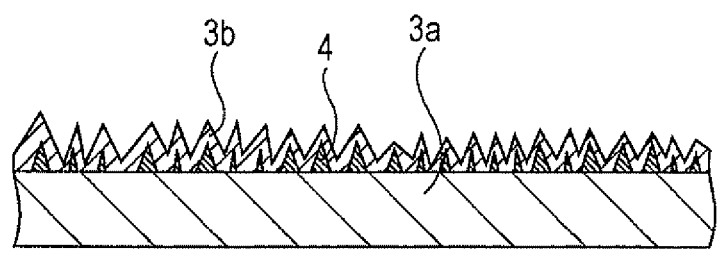

In a modification of the embodiment, as shown in FIG. 2B, inclusions 4 are provided on the surface of each tungsten wire 3a, after which each noble metal plating layer 3b is formed thereon. This makes it possible to form the surface of each noble metal plating layer 3b with the first uneven shape. Since the inclusions 4 exist in protrusions of the first uneven shape, it is possible to easily form the first uneven shape. The inclusions 4 may be disposed over the entire length of the tungsten wires 3a, or may be disposed on portions of the tungsten wires 3a in a longitudinal direction or a circumferential direction thereof.

Examples of methods of forming the inclusions 4 include sputtering, spraying, and laser abrasion. Examples of materials of the inclusions 4 include metals, such as stainless steel, and ceramic. The materials are not limited thereto, so that other materials may be used for the inclusions 4.

Next, using FIGS. 3A and 3B, a guidewire II according to an embodiment will be described by focusing on the differences between the guidewire 11 according to an embodiment and the guidewire 1 according to the above-discussed embodiment. Portions that correspond to those in the above-discussed embodiment will be given the same reference numerals in FIG. 3.

Figure 3A:
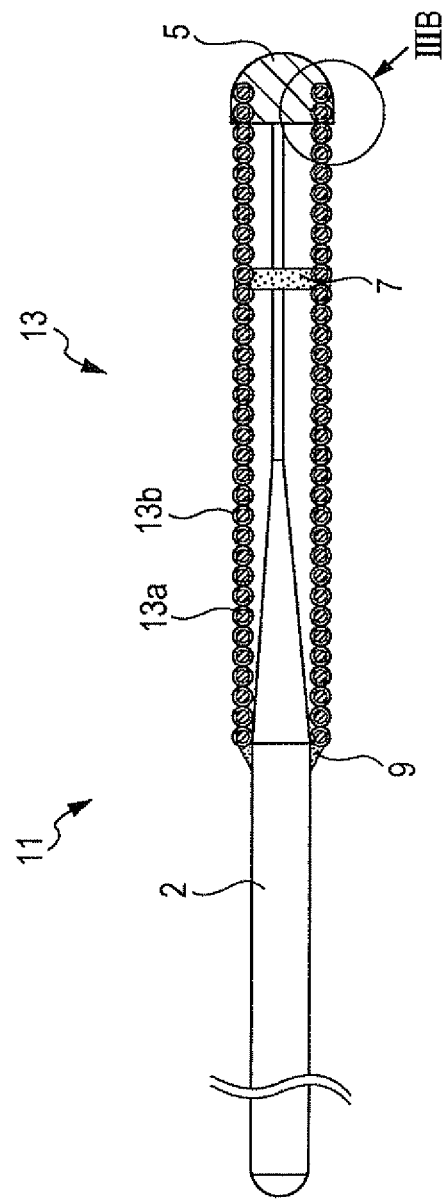
FIGS. 3A and 3B illustrate a structure according to an embodiment of the present invention, with FIG. 3A being an overall view of a guidewire and FIG. 3B being an enlarged transverse cross-sectional view of only wires of a coil body at a portion IIIB shown in FIG. 3A.

In FIG. 3A, for facilitating understanding, a lengthwise direction of the guidewire 1 is reduced, and the entire guidewire 11 is schematically illustrated, so that the dimensions of the entire guidewire 11 differ from the actual dimensions thereof.

FIG. 3A is an overall view of the guidewire 11, and FIG. 38 is an enlarged view of a portion MB shown in FIG. 3A. For convenience of explanation, only wires of the coil body 13 are shown, that is, the wire are shown without a tip portion 5. From FIGS. 3A and 3B, it can be seen that a coil body 13 of the guidewire 11 differs from the coil body 3 of the guidewire 1 according to the above-discussed embodiment in that surfaces of tungsten wires 13a each having a second uneven shape are covered by corresponding noble metal plating layers 13b.

Figure 3B:
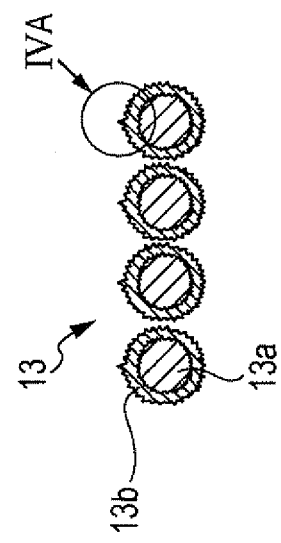
Figure 4A:
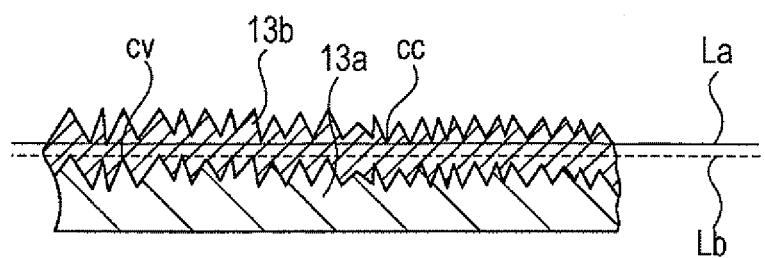
FIGS. 4A to 4C illustrate the structure according to an embodiment of the present invention, with FIG. 4A being an enlarged view of a portion IVA shown in FIG. 3B, FIG. 4B illustrating a modification of the embodiment and being an enlarged view of the portion IVA shown in FIG. 3B, and FIG. 4C being an enlarged view of a portion IVC shown in FIG. 4B.

FIG. 4A is an enlarged view of a portion IVA shown in FIG. 3B (that is, an enlarged view of one of the coil wires in transverse cross section). For convenience of explanation, the coil wire is shown as having a flat surface instead of an arc-shaped surface. As is clear from FIG. 4A, the positions of recesses and protrusions in the second uneven shape of each tungsten wire 13a correspond to the positions of recesses and protrusions in the first uneven shape of the surface of each noble metal plating layer 13b in transverse cross section of each coil wire. That is, in transverse cross section of each coil wire, the protrusions in the second uneven shape and the protrusions in the first uneven shape are formed in correspondence with each other, and the recesses in the second uneven shape and the recesses in the first uneven shape are formed in correspondence with each other.

Depending upon the plating method of the noble metal plating layers 13b and the method of forming the coil body 13, when, for example, each protrusion in the first uneven shape is ground, there may no longer be, in transverse cross section of each coil wire, any recess in the second uneven shape whose position completely corresponds to that of a recess in the first uneven shape, or any protrusion in the second uneven shape whose position completely corresponds to that of a protrusion in the first uneven shape. However, all that is required is for the position of at least one recess in the second uneven shape and the position of at least one recess in the first uneven shape to correspond to each other, or for the position of at least one protrusion in the second uneven shape and the position of at least one protrusion in the first uneven shape to correspond to each other. It is most desirable that, in transverse cross section of each coil wire, the positions of the recesses in the second uneven shape and the positions of the recesses in the first uneven shape correspond to each other over the entire length of each coil wire, and the positions of the protrusions in the second uneven shape and the positions of the protrusions in the first uneven shape correspond to each other over the entire length of each coil wire.

Accordingly, in the guidewire 11 according to the embodiment, the surface of each tungsten wire 13a has the second uneven shape. In addition, in transverse cross section of each coil wire (tungsten wire 13a+noble metal plating layer 13b), the positions of the recesses in the first uneven shape of the noble metal plating layer 13h correspond to the positions of the recesses in the second uneven shape, and the positions of the protrusions in the first uneven shape of the noble metal plating layer 13b correspond to the positions of the protrusions in the second uneven shape. Therefore, the noble metal plating layers 13b are prevented from separating from the tungsten wires 13a by the anchoring effect, and it is possible to considerably increase the bonding strength between the core shaft 2 and the coil body 13, and, thus, significantly prevent the coil body 13 from separating from the core shaft 2 because the metal solder also has an anchoring effect with respect to the noble metal plating layer 13b.

As shown in FIG. 4A, the guidewire 11 according to the embodiment is such that a line La passing through at least two of the lowest recesses (i.e., the lowest portion cc) in the first uneven shape is positioned closer to an outer side of the coil body 13 than a line Lb passing through at least two of the highest protrusions (i.e., the highest portion cv) in the second uneven shape. That is, the lowest recesses in the first uneven shape are closer to the outer surface of the coil body than the highest protrusions in the second uneven shape.

Figure 4B:
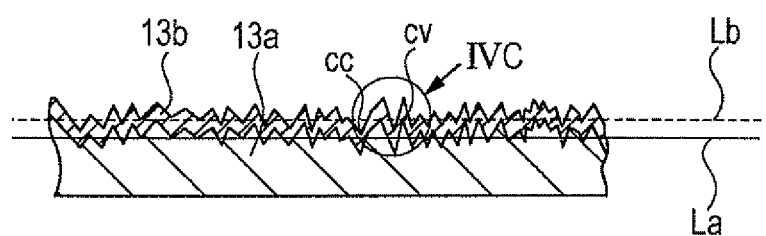
Figure 4C:
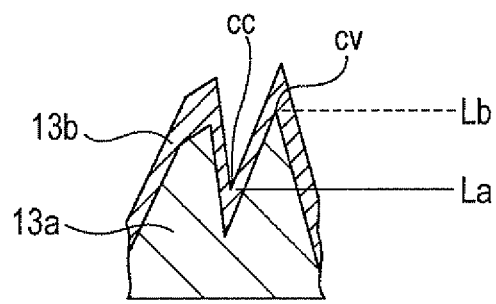

FIG. 4B illustrates a modification of the above-discussed embodiment, and FIG. 4C is an enlarged view of a portion IVC shown in FIG. 413. As is clear from FIGS. 4B and 4C, a line La passing through at least two of the lowest recesses (i.e., the lowest portion cc) in a first uneven shape may be positioned closer to the center of a coil wire of the coil body 13 than a line Lb passing through at least two of the highest protrusions (i.e., the highest portion cv) in a second uneven shape. That is, the lowest recesses in the first uneven shape are closer to the center of the coil wire of the coil body 13 than the highest protrusions in the second uneven shape.

In transverse cross section of the coil wire, the lowest portion cc of the recess in the first uneven shape is positioned closer to the center of the coil wire than the highest portion cv of the protrusion in the second uneven shape. Consequently, it is possible to further prevent the noble metal plating layer 13b from separating from the corresponding tungsten wire 13a, to considerably increase the bonding strength between the core shaft 2 and the coil body 13, and thus reliably prevent the coil body 13 from separating from the core shaft 2.

Next, with reference to FIG. 5, a guidewire 21 according to an embodiment will be described focusing on the differences between the guidewire 21 according to the embodiment and the guidewire 11 according to the above discussed embodiment. Portions that correspond to those in the above-discussed embodiment will be given the same reference numerals in FIG. 5.

Figure 5:
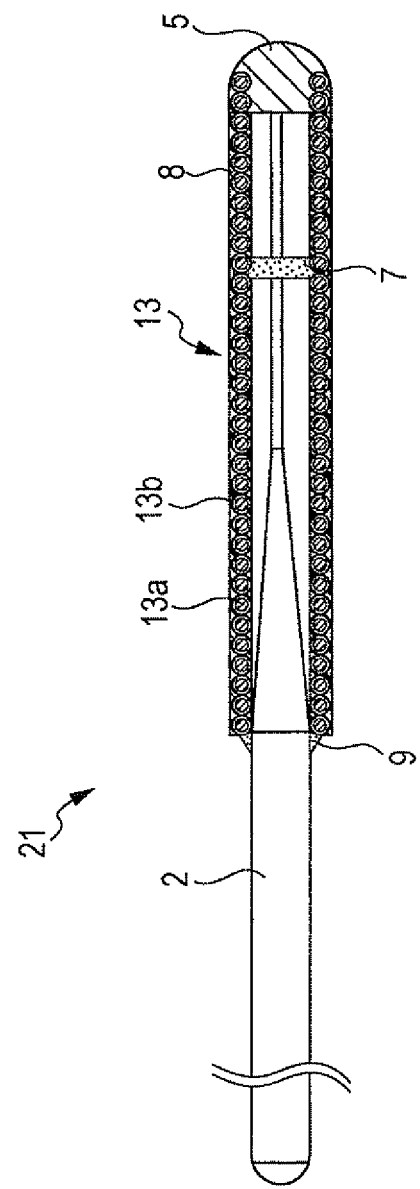
FIG. 5 is an overall view of an embodiment of the present invention.

In FIG. 5, for facilitating understanding, a lengthwise direction of the guidewire 21 is reduced, and the entire guidewire 21 is schematically illustrated, so that the dimensions of the entire guidewire 21 differ from the actual dimensions thereof.

FIG. 5 is an overall view of the guidewire 21. A coil body 13 includes tungsten wires 13a each having a second uneven shape and noble metal plating layers 13b covering outer peripheries of the tungsten wires 13a. An outer surface and an inner surface of the coil body 13 are coated with a lubricant coating agent 8 so as to be covered by the lubricant coating agent.

Accordingly, in the guidewire 21 according to the embodiment, the outer surface and the inner surface of the coil body 13 are coated with the lubricant coating agent 8. Therefore, even if a surface of the coil body 13 contacts a contact portion (such as the interior of a catheter or a blood vessel), the coil body 13 slides easily with respect to the contact portion. Consequently, the addition of stress to the coil body 13 in a shearing direction thereof can be reduced, so that it is possible to prevent the coil body 13 from separating from the core shaft 2. Further, since the surface of the coil body 13 has a first uneven shape, it is possible to prevent the lubricant coating agent 8, provided at the coil body 13, from separating from the surface of the coil body 13 by an anchoring effect. As a result, it is possible to maintain the lubricating ability of the lubricant coating agent 8.

By maintaining the lubricating ability of the lubricant coating agent 8, it is possible to reduce for a long period of time friction resistance of a portion where the coil body 13 and the contact portion contact each other. Therefore, it is possible to reliably prevent the coil body 13 from separating from the core shaft 2.

As illustrated in FIG. 5, from the viewpoint of protecting the coil body 13, it is desirable for the lubricant coating agent 8 to be applied to the outer surface and the inner surface of the coil body 13. However, the lubricant coating agent 8 may be applied to only the outer surface of the coil body 13.

As illustrated in FIG. 5, from the viewpoint of maximally preventing the coil body 13 from being separated from the core shaft 2, it is desirable to apply the lubricant coating agent 8 over the entire length of the coil body 13. However, the lubricant coating agent 8 may be applied to only a portion of the coil body 13 in a long-axis direction thereof (such as a distal end of the coil body 13).

Examples of materials of the lubricant coating agent 8 include fluorocarbon resin such as polytetrafluoroethylene, silicone oil such as polydimethylsiloxane, and hydrophilic resin such as polyvinyl pyrrolidone, polyacrylamide, and hyaluronic acid. However, the materials are not limited thereto, so that other materials may also be used.

Various elastomer resins, such as polyamide elastomer or polyurethane elastomer, may be thinly applied to the outer periphery of the coil body 13 of the guidewire 21, and the aforementioned hydrophilic resin may be applied to the outer periphery of the elastomer resin. Even in such a case, the lubricating ability of the lubricant coating agent 8 is maintained.

When the elastomer resin is thinly applied, it is desirable that the surface of the elastomer resin after being applied to the outer periphery of the coil body 13 have a slight third uneven shape based on the first uneven shape. This allows the lubricating ability of the lubricant coating agent 8 formed of hydrophilic resin applied to the surface of the elastomer resin to be maintained for a long period of time by an anchoring effect of the third uneven shape.

The present invention is not limited to the above-described embodiments. Various modifications can be made by those skilled in the art within the technical idea of the present invention.

For example, it is possible to apply the inclusions 4 used in the modification of the above-discussed embodiment to the coil body 13 according to the above-discussed embodiment. This makes it possible to make more complex the first uneven shape, and facilitate manufacturing of the complex uneven shape.

The heights of the protrusions and the depths of the recesses in the first uneven shape and in the second uneven shape may be made the same. However, considering the bonding strength between the tungsten wires 13*a* and the noble metal plating layers 13*b* and the bonding strength between the noble metal plating layers 3*b* or 13*b* with respect to the metal solder by the anchoring effect, it is desirable that the heights of the protrusions and the depths of the recesses in the first uneven shape and in the second uneven shape differ from each other.

In order to increase the bonding strength between the tungsten wires 3*a* and 13*a* and the respective noble metal plating layers 3*b* and 13*b*, metal plating layers formed of other metals may be provided as binders.

While the disclosed embodiments have been shown and described in detail, the foregoing description is in all aspects illustrative and not restrictive. It is therefore understood that numerous modifications and variations can be devised without departing from the spirit and scope of the invention.

What is claimed is:

1. A guidewire comprising:
a core shaft;
a coil body that includes a tungsten wire and a noble metal plating layer that covers at least a portion of a surface of the tungsten wire, the coil body covering the core shaft; and
a joining portion formed of metal solder that couples the core shaft and the coil body, wherein
a surface of the noble metal plating layer has a first uneven shape including at least one recess and at least one protrusion, and
the surface of the noble metal plating layer has the first uneven shape in a transverse cross-sectional view of a coil wire of the coil body.

2. A guidewire comprising:
a core shaft;
a coil body that includes a tungsten wire and a noble metal plating layer that covers at least a portion of a surface of the tungsten wire, the coil body covering the core shaft; and
a joining portion formed of metal solder that couples the core shaft and the coil body, wherein
a surface of the noble metal plating layer has a first uneven shape including at least one recess and at least one protrusion,
the surface of the tungsten wire has a second uneven shape including at least one recess and at least one protrusion, and
in a transverse cross-sectional view of a coil wire of the coil body, a position of the at least one recess in the first uneven shape corresponds to a position of the at least one recess in the second uneven shape.

3. The guidewire according to claim 2, wherein
a position of a majority of the at least one recess in the first uneven shape corresponds to a position of a majority of the at least one recess in the second uneven shape.

4. The guidewire according to claim 2, wherein
a position of substantially all of the at least one recess in the first uneven shape corresponds to a position of substantially all of the at least one recess in the second uneven shape.

* * * * *